United States Patent [19]

Fleischle

[11] Plant 4,948

[45] Nov. 16, 1982

[54] DISTINCT VARIETY OF STREPTOCARPUS NAMED HERA

[75] Inventor: Gerhard Fleischle, Vaihingen, Fed. Rep. of Germany

[73] Assignee: Oglevee Associates, Inc., Connellsville, Pa.

[21] Appl. No.: 204,350

[22] Filed: Nov. 5, 1980

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Webb, Burden, Robinson & Webb

[57] ABSTRACT

A new variety of Streptocarpus plant is characterized by its blue flower having dark violet striping extending in a yellow throat area. It is a small compact plant and is generally nonfertile.

1 Drawing Figure

BACKGROUND OF THE NEW PLANT

The present invention comprises a new and distinct cultivar of streptocarpus × hybridus known by the varietal name Hera. The new cultivar is a mutation achieved through irradiation of Greta, formerly named Helle Glocke (U.S. Pat. No. 4,522).

The new cultivar is most similar to Greta. However, Hera is smaller, having shorter leaves, more blooms and smaller blooms. In addition, it is earlier flowering and the flowers have less violet and more blue coloring than Greta. The throat area has less striping.

The new cultivar was discovered in 1979 in Vaihingen, Federal Republic of Germany; was first asexually reproduced by cuttings in Vaihingen, Federal Republic of Germany; and has been asexually reproduced by cuttings of Oglevee Floral Company in Connellsville, Pa. It has been found to retain its distinctive characteristics through successive propagations.

DESCRIPTION OF THE DRAWING

The accompanying drawing illustrates the new cultivar.

DESCRIPTION OF THE NEW PLANT

The following detailed description sets forth the characteristics of the new cultivar. The data which defines these characteristics were collected from asexual reproductions carried out by Gerhard Fleischle in Vaihingen, Federal Republic of Germany. Color references are primarily to the R.H.S. color chart of the Royal Horticultural Society of London unless otherwise referenced. The color references were collected from asexual reproductions carried out by Oglevee Floral Company in Connellsville, Pa.

Botanical classification: Gesneriaceae (Family); *Streptocarpus* × *Hybridus* (Genus × Species).

Flower:

- *Fully expanded.*—Five centimeters.
- *Borne.*—In clusters of one to eight flowers per stalk above foliage. Flower stalks arise from mid-rib of each leaf.
- *Stems.*—Single, long and pubescent.
- *Form.*—Funnel formed in an umbel.

Color:

- *Front of petals.*—Fan 2 Violet Group 88-B.
- *Throat.*—Fan 1 Yellow Group 6-D with a plurality of stripes, Fan 2 Purple Group 79-A, extending all the way into the center.
- *Base of petals.*—Fan 2 Violet Group 88-C.
- *Reverse of petals.*—Fan 2 Violet Group 87-B.
- *Tonality from a distance.*—Exotica 53 purplish blue. Less violet and more blue than Helle Glocke, less throat striping.
- *Discoloration.*—Insignificant.

Petals:

- *Texture.*—Velvet.
- *Appearance.*—Individually lobed with smooth margin.
- *Arrangement.*—Regularly united into an elliptical form.
- *Fragrance.*—None.

Reproductive organs:

- *Anthers.*—Two per flower and interconnected.
- *Pollen.*—Generally nonfertile.

Plant:

- *Form.*—Leaves rosulete from a crown at the soil line.
- *Growth.*—A spreading, free flowing habit with leaf bases being acute.
- *Height from soil line.*—12 to 18 centimeters.
- *Spread.*—30 to 35 centimeters.

Foliage:

- *Size.*—Approximately 15 to 18 centimeters in length and 5 to 8 centimeters in width at the widest point.
- *Quantity.*—10 to 18 leaves.
- *Top side.*—Fan 3 Green Group 137-C.
- *Underside.*—Fan 3 Yellow-Green Group 145-B.
- *Rib and vein color.*—Fan 3 Green Group 138-D.
- *Shape.*—Oblanceolete.
- *Ribs and veins.*—Pinnate.
- *Margin.*—Ruffled margin with crenate serrations.
- *Stipules.*—None.

I claim:

1. A new and distinct variety of Streptocarpus substantially as herein shown and described.

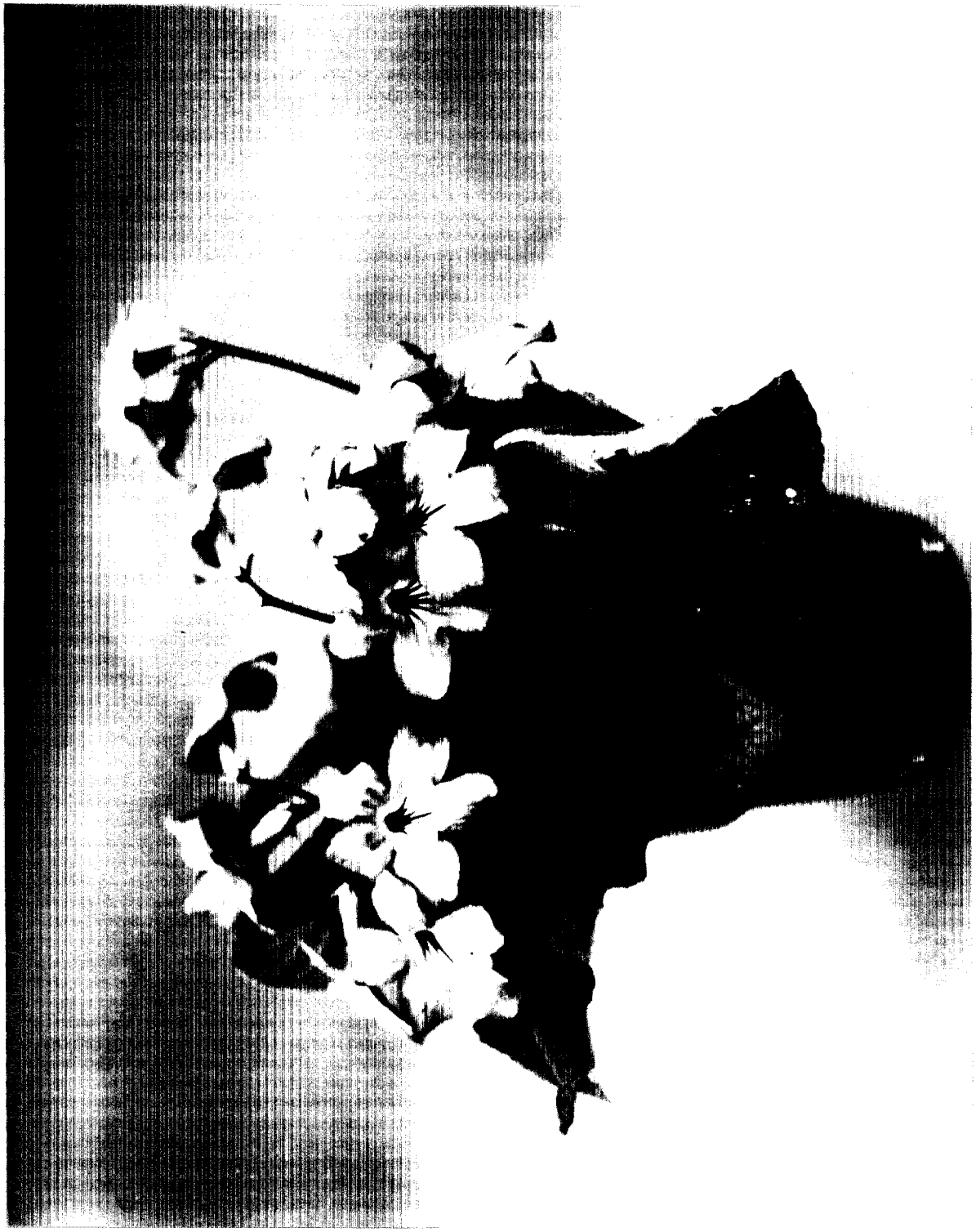

* * * * *